(12) United States Patent
Lee et al.

(10) Patent No.: US 9,970,035 B2
(45) Date of Patent: May 15, 2018

(54) METHODS FOR PRODUCING BIODIESEL BY RECOMBINANT LIPASE

(71) Applicant: NATIONAL TAIWAN NORMAL UNIVERSITY, Taipei (TW)

(72) Inventors: Guan-Chiun Lee, Taipei (TW); Ting-Chun Kuo, Taipei (TW)

(73) Assignee: National Taiwan Normal University, Taipei (TW)

(*) Notice: Subject to any disclaimer, the term of this patent is extended or adjusted under 35 U.S.C. 154(b) by 6 days.

(21) Appl. No.: 15/135,317

(22) Filed: Apr. 21, 2016

(65) Prior Publication Data

US 2017/0137850 A1 May 18, 2017

(30) Foreign Application Priority Data

Nov. 17, 2015 (TW) .................................. 104137833

(51) Int. Cl.
*C12P 7/64* (2006.01)

(52) U.S. Cl.
CPC .................................... *C12P 7/649* (2013.01)

(58) Field of Classification Search
None
See application file for complete search history.

(56) References Cited

PUBLICATIONS

Sagiroglu. Artif Cells Blood Substit Immobil Biotechnol. 2008;36(2):138-49.*
Accession P20261. Feb. 1, 1991.*
Accession P32946. Oct. 1, 1993.*
Accession P32947. Oct. 1, 1993.*
Accession P32948. Oct. 1, 1993.*
Gupta et al. Research Journal of Microbiology (2011), 6(3), 281-288.*
Azocar et al. Appl Microbiol Biotechnol. Oct. 2010;88(3):621-36.*
"Conversion of crude Jatropha Curcas seed oil into biodiesel using liquid recombinant Candida regose lipase isoqymes", Bioresource technology 192, pp. 54-59, May 19, 2015.
"Enhanced expression of recombinant Candida regose lipase 2 in Pichia pastoris and its application in biodiesel production", Thesis, Jul. 21, 2015.
Abdulla, R., et al., "Biodiesel production from Jatropha curcas: a critical review. Crit Rev Biotechnol", vol. 31, pp. 53-64, 2011.
Chang, S.W., et al., "Codon optimization of Candida rugosa lip1 gene for improving expression in Pichia pastoris and biochemical characterization of the purified recombinant LIP1 lipase", J Agric Food Chem, pp. 815-822, 2006.
Chang, S.W., "Efficient production of active recombinant Candida rugosa LIP3 lipase in Pichia pastoris and biochemical characterization of the purified enzyme", J Agric Food Chem, pp. 5831-5838, 2006.
Chang, S.W., "Engineering the expression and biochemical characteristics of recombinant Candida rugosa LIP2 lipase by removing the additional N-terminal peptide and regional codon optimization", J Agric Food Chem, pp. 6710-6719, 2011.
Chang S.W., et al., "Simultaneous production of fatty acid methyl esters and diglycerides by four recombinant Candida rugosa lipase's isozymes", Food Chem, pp. 140-145, 2014.
De Oliveira, J.S., "Characteristics and composition of Jatropha gossypiifoliaand *Jatropha curcas* L. oils and application for biodiesel production. Biomass and Bioenergy", vol. 33, pp. 449-453, 2009.
Hama, S, et al., "Enzymatic biodiesel production: an overview of potential feedstocks and process development. Bioresour Technol", vol. 135, pp. 386-395, 2013.
Kawakami, K., "Application of a Burkholderia cepacia lipase-immobilized silica monolith to batch and continuous biodiesel production with a stoichiometric mixture of methanol and crude Jatropha oil. Biotechnol Biofuels", vol. 4, pp. 42, 2011.
Lee, G.C., "Multiple mutagenesis of non-universal serine codons of the Candida rugosa LIP2 gene and biochemical characterization of purified recombinant LIP2 lipase overexpressed in Pichia pastoris", Biochem J., pp. 603-611, 2002.
Longhi, S., "Cloning and nucleotide sequences of two lipase genes from Candida cylindracea.", 1131, pp. 227-232, 1992.
Lotti, M., "Cloning and analysis of Candida cylindracea lipase sequences", 124, pp. 45-55, 1993.
Moser, B.R., "Influence of Blending Canola, Palm, Soybean, and Sunflower Oil Methyl Esters on Fuel Properties of Biodiesel", Energy Fuels, pp. 4301-4306, 2008.
Park, E.Y., et al., "Lipase-catalyzed biodiesel production from waste activated bleaching earth as raw material in a pilot plant.", vol. 99, pp. 3130-3135, 2008.
Ranganathan, S.V., "An overview of enzymatic production of biodiesel", Bioresour Technol, pp. 3975-3981, 2008.
Shah et al, "Biodiesel Preparation by Lipase-Catalyzed Transesterification of Jatropha Oil", Energy & Fuels, pp. 154-159, 2004.
Shah, S., "Lipase catalyzed preparation of biodiesel from Jatropha oil in a solvent free system.", Process Biochem, pp. 409-414, 2007.
Tang, S.J., "Recombinant expression and characterization of the Candida rugosa lip4 lipase in Pichia pastoris: comparison of glycosylation, activity, and stability", Arch Biochem Biophys, pp. 93-98, 2001.
Wang, Y., "Highly-efficient enzymatic conversion of crude algal oils into biodiesel", Bioresour Technol, pp. 143-149, 2014.
You, Q., "Biodiesel production from Jatropha oil catalyzed by immobilized Burkholderia cepacia lipase on modified attapulgite", Bioresour Technol, pp. 202-207, 2013.
Conversion of Crude Jatropha Curcas Seed Oil Into Biodiesel using liquid Recombinant Candida Regose Lipase Isoqymes, Bioresource Technology, May 19, 2015.
Enhanced Expression of Recombinant Candida Regose Lipase 2 in Pichia Pastoris and Its Application in Biodiesel Production, Thesis, Jul. 21, 2015.

* cited by examiner

*Primary Examiner* — Christian Fronda
(74) *Attorney, Agent, or Firm* — Kramer Amado P.C.

(57) ABSTRACT

A method for producing biodiesel is provided, which includes providing a recombinant *Candida rugosa* lipase; reacting the recombinant *C. rugosa* lipase and a non-edible oil; and isolating the biodiesel from the reacted solution.

19 Claims, 5 Drawing Sheets

SEQUENCE LISTING

```
<160> NUMBER OF SEQ ID NOS: 8

<210> SEQ ID NO 1
<211> LENGTH: 534
<212> TYPE: PRT
<213> ORGANISM: Candida rugosa

<400> SEQUENCE: 1

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asp Gly Gln Lys Phe Thr Ser Tyr Gly Pro Ser Cys Met Gln Gln Asn
    50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Val Gly
        115                 120                 125

Gly Thr Ser Thr Phe Pro Pro Ala Gln Met Ile Thr Lys Ser Ile Ala
    130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
    210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Phe Asp Leu Leu Ala Ser Asn Ala Gly Cys Gly Ser Ala Ser
```

```
                260                 265                 270
Asp Lys Leu Ala Cys Leu Arg Gly Val Ser Ser Asp Thr Leu Glu Asp
        275                 280                 285
Ala Thr Asn Asn Thr Pro Gly Phe Leu Ala Tyr Ser Ser Leu Arg Leu
    290                 295                 300
Ser Tyr Leu Pro Arg Pro Asp Gly Val Asn Ile Thr Asp Asp Met Tyr
305                 310                 315                 320
Ala Leu Val Arg Glu Gly Lys Tyr Ala Asn Ile Pro Val Ile Ile Gly
                325                 330                 335
Asp Gln Asn Asp Glu Gly Thr Phe Phe Gly Thr Ser Ser Leu Asn Val
        340                 345                 350
Thr Thr Asp Ala Gln Ala Arg Glu Tyr Phe Lys Gln Ser Phe Val His
    355                 360                 365
Ala Ser Asp Ala Glu Ile Asp Thr Leu Met Thr Ala Tyr Pro Gly Asp
370                 375                 380
Ile Thr Gln Gly Ser Pro Phe Asp Thr Gly Ile Leu Asn Ala Leu Thr
385                 390                 395                 400
Pro Gln Phe Lys Arg Ile Ser Ala Val Leu Gly Asp Leu Gly Phe Thr
                405                 410                 415
Leu Ala Arg Arg Tyr Phe Leu Asn His Tyr Thr Gly Thr Lys Tyr
        420                 425                 430
Ser Phe Leu Ser Lys Gln Leu Ser Gly Leu Pro Val Leu Gly Thr Phe
    435                 440                 445
His Ser Asn Asp Ile Val Phe Gln Asp Tyr Leu Leu Gly Ser Gly Ser
    450                 455                 460
Leu Ile Tyr Asn Asn Ala Phe Ile Ala Phe Ala Thr Asp Leu Asp Pro
465                 470                 475                 480
Asn Thr Ala Gly Leu Leu Val Lys Trp Pro Glu Tyr Thr Ser Ser Ser
                485                 490                 495
Gln Ser Gly Asn Asn Leu Met Met Ile Asn Ala Leu Gly Leu Tyr Thr
        500                 505                 510
Gly Lys Asp Asn Phe Arg Thr Ala Gly Tyr Asp Ala Leu Phe Ser Asn
        515                 520                 525
Pro Pro Ser Phe Phe Val
        530

<210> SEQ ID NO 2
<211> LENGTH: 534
<212> TYPE: PRT
<213> ORGANISM: Candida rugosa

<400> SEQUENCE: 2

Val Pro Thr Ala Thr Leu Ala Asn Gly Asp Thr Ile Thr Gly Leu Asn
1               5                   10                  15
Ala Ile Val Asn Glu Lys Phe Leu Gly Ile Pro Phe Ala Glu Pro Pro
            20                  25                  30
Val Gly Ser Leu Arg Phe Lys Pro Pro Val Pro Tyr Ser Ala Ser Leu
        35                  40                  45
Asn Gly Gln Gln Phe Thr Ser Tyr Gly Pro Ser Cys Met Gln Met Asn
    50                  55                  60
Pro Met Gly Ser Phe Glu Asp Thr Leu Pro Lys Asn Ala Leu Asp Leu
65              70                  75                  80
Val Leu Gln Ser Lys Ile Phe Gln Val Val Leu Pro Asn Asp Glu Asp
                85                  90                  95
```

```
Cys Leu Thr Ile Asn Val Ile Arg Pro Pro Gly Thr Arg Ala Ser Ala
                100                 105                 110
Gly Leu Pro Val Met Leu Trp Ile Phe Gly Gly Phe Glu Leu Gly
    115                 120                 125
Gly Ser Ser Leu Phe Pro Gly Asp Gln Met Val Ala Lys Ser Val Leu
    130                 135                 140
Met Gly Lys Pro Val Ile His Val Ser Met Asn Tyr Arg Val Ala Ser
145                 150                 155                 160
Trp Gly Phe Leu Ala Gly Pro Asp Ile Gln Asn Glu Gly Ser Gly Asn
                165                 170                 175
Ala Gly Leu His Asp Gln Arg Leu Ala Met Gln Trp Val Ala Asp Asn
                180                 185                 190
Ile Ala Gly Phe Gly Gly Asp Pro Ser Lys Val Thr Ile Tyr Gly Glu
                195                 200                 205
Ser Ala Gly Ser Met Ser Thr Phe Val His Leu Val Trp Asn Asp Gly
    210                 215                 220
Asp Asn Thr Tyr Asn Gly Lys Pro Leu Phe Arg Ala Ala Ile Met Gln
225                 230                 235                 240
Ser Gly Cys Met Val Pro Ser Asp Pro Val Asp Gly Thr Tyr Gly Thr
                245                 250                 255
Glu Ile Tyr Asn Gln Val Val Ala Ser Ala Gly Cys Gly Ser Ala Ser
                260                 265                 270
Asp Lys Leu Ala Cys Leu Arg Gly Leu Ser Gln Asp Thr Leu Tyr Gln
    275                 280                 285
Ala Thr Ser Asp Thr Pro Gly Val Leu Ala Tyr Pro Ser Leu Arg Leu
    290                 295                 300
Ser Tyr Leu Pro Arg Pro Asp Gly Thr Phe Ile Thr Asp Asp Met Tyr
305                 310                 315                 320
Ala Leu Val Arg Asp Gly Lys Tyr Ala His Val Pro Val Ile Ile Gly
                325                 330                 335
Asp Gln Asn Asp Glu Gly Thr Leu Phe Gly Leu Ser Ser Leu Asn Val
                340                 345                 350
Thr Thr Asp Ala Gln Ala Arg Ala Tyr Phe Lys Gln Ser Phe Ile His
    355                 360                 365
Ala Ser Asp Ala Glu Ile Asp Thr Leu Met Ala Ala Tyr Thr Ser Asp
    370                 375                 380
Ile Thr Gln Gly Ser Pro Phe Asp Thr Gly Ile Phe Asn Ala Ile Thr
385                 390                 395                 400
Pro Gln Phe Lys Arg Ile Ser Ala Leu Leu Gly Asp Leu Ala Phe Thr
                405                 410                 415
Leu Ala Arg Arg Tyr Phe Leu Asn Tyr Gln Gly Gly Thr Lys Tyr
                420                 425                 430
Ser Phe Leu Ser Lys Gln Leu Ser Gly Leu Pro Val Leu Gly Thr Phe
    435                 440                 445
His Gly Asn Asp Ile Ile Trp Gln Asp Tyr Leu Val Gly Ser Gly Ser
    450                 455                 460
Val Ile Tyr Asn Asn Ala Phe Ile Ala Phe Ala Asn Asp Leu Asp Pro
465                 470                 475                 480
Asn Lys Ala Gly Leu Trp Thr Asn Trp Pro Thr Tyr Thr Ser Ser Ser
                485                 490                 495
Gln Ser Gly Asn Asn Leu Met Gln Ile Asn Gly Leu Gly Leu Tyr Thr
                500                 505                 510
Gly Lys Asp Asn Phe Arg Pro Asp Ala Tyr Ser Ala Leu Phe Ser Asn
```

```
              515                 520                 525
Pro Pro Ser Phe Phe Val
        530

<210> SEQ ID NO 3
<211> LENGTH: 534
<212> TYPE: PRT
<213> ORGANISM: Candida rugosa

<400> SEQUENCE: 3

Ala Pro Thr Ala Lys Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asn Gly Gln Lys Phe Thr Ser Tyr Gly Pro Ser Cys Met Gln Gln Asn
    50                  55                  60

Pro Glu Gly Thr Phe Glu Glu Asn Leu Gly Lys Thr Ala Leu Asp Leu
65                  70                  75                  80

Val Met Gln Ser Lys Val Phe Gln Ala Val Leu Pro Gln Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Ile Gly
        115                 120                 125

Ser Pro Thr Ile Phe Pro Pro Ala Gln Met Val Thr Lys Ser Val Leu
    130                 135                 140

Met Gly Lys His Ile Ile His Val Ala Val Asn Tyr Arg Val Ala Ser
145                 150                 155                 160

Trp Gly Phe Leu Ala Gly Asp Asp Ile Lys Ala Glu Gly Ser Gly Asn
                165                 170                 175

Ala Gly Leu Lys Asp Gln Arg Leu Gly Met Gln Trp Val Ala Asp Asn
            180                 185                 190

Ile Ala Gly Phe Gly Gly Asp Pro Ser Lys Val Thr Ile Phe Gly Glu
        195                 200                 205

Ser Ala Gly Ser Met Ser Val Leu Cys His Leu Ile Trp Asn Asp Gly
    210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Pro Val Asp Gly Thr Tyr Gly Asn
                245                 250                 255

Glu Ile Tyr Asp Leu Phe Val Ser Ser Ala Gly Cys Gly Ser Ala Ser
            260                 265                 270

Asp Lys Leu Ala Cys Leu Arg Ser Ala Ser Ser Asp Thr Leu Leu Asp
        275                 280                 285

Ala Thr Asn Asn Thr Pro Gly Phe Leu Ala Tyr Ser Ser Leu Arg Leu
    290                 295                 300

Ser Tyr Leu Pro Arg Pro Asp Gly Lys Asn Ile Thr Asp Asp Met Tyr
305                 310                 315                 320

Lys Leu Val Arg Asp Gly Lys Tyr Ala Ser Val Pro Val Ile Ile Gly
                325                 330                 335

Asp Gln Asn Asp Glu Gly Thr Ile Phe Gly Leu Ser Ser Leu Asn Val
            340                 345                 350
```

```
Thr Thr Asn Ala Gln Ala Arg Ala Tyr Phe Lys Gln Ser Phe Ile His
            355                 360                 365

Ala Ser Asp Ala Glu Ile Asp Thr Leu Met Ala Ala Tyr Pro Gln Asp
370                 375                 380

Ile Thr Gln Gly Ser Pro Phe Asp Thr Gly Val Leu Asn Ala Leu Thr
385                 390                 395                 400

Pro Gln Phe Lys Arg Ile Ser Ala Val Leu Gly Asp Leu Ala Phe Ile
                405                 410                 415

His Ala Arg Arg Tyr Phe Leu Asn His Phe Gln Gly Gly Thr Lys Tyr
                420                 425                 430

Ser Phe Leu Ser Lys Gln Leu Ser Gly Leu Pro Ile Met Gly Thr Phe
            435                 440                 445

His Ala Asn Asp Ile Val Trp Gln Asp Tyr Leu Leu Gly Ser Gly Ser
            450                 455                 460

Val Ile Tyr Asn Asn Ala Phe Ile Ala Phe Ala Thr Asp Leu Asp Pro
465                 470                 475                 480

Asn Thr Ala Gly Leu Leu Val Asn Trp Pro Lys Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Met Thr Asn
            515                 520                 525

Pro Ser Ser Phe Phe Val
            530

<210> SEQ ID NO 4
<211> LENGTH: 534
<212> TYPE: PRT
<213> ORGANISM: Candida rugosa

<400> SEQUENCE: 4

Val Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Gln Pro Pro
                20                  25                  30

Val Gly Asn Leu Arg Phe Lys Pro Pro Val Pro Tyr Ser Ala Ser Leu
            35                  40                  45

Asn Gly Gln Lys Phe Thr Ser Tyr Gly Pro Ser Cys Met Gln Met Asn
        50                  55                  60

Pro Leu Gly Asn Trp Asp Ser Ser Leu Pro Lys Ala Ala Ile Asn Ser
65                  70                  75                  80

Leu Met Gln Ser Lys Leu Phe Gln Ala Val Leu Pro Asn Gly Glu Asp
                85                  90                  95

Cys Leu Thr Ile Asn Val Val Arg Pro Ser Gly Thr Lys Pro Gly Ala
            100                 105                 110

Asn Leu Pro Val Met Val Trp Ile Phe Gly Gly Gly Phe Glu Val Gly
            115                 120                 125

Gly Ser Ser Leu Phe Pro Pro Ala Gln Met Ile Thr Ala Ser Val Leu
130                 135                 140

Met Gly Lys Pro Ile Ile His Val Ser Met Asn Tyr Arg Val Ala Ser
145                 150                 155                 160

Trp Gly Phe Leu Ala Gly Pro Asp Ile Lys Ala Glu Gly Ser Gly Asn
                165                 170                 175

Ala Gly Leu His Asp Gln Arg Leu Gly Leu Gln Trp Val Ala Asp Asn
            180                 185                 190
```

Ile Ala Gly Phe Gly Gly Asp Pro Ser Lys Val Thr Ile Phe Gly Glu
            195                 200                 205

Ser Ala Gly Ser Met Ser Val Met Cys Gln Leu Leu Trp Asn Asp Gly
    210                 215                 220

Asp Asn Thr Tyr Asn Gly Lys Pro Leu Phe Arg Ala Ile Met Gln
225                 230                 235                 240

Ser Gly Ala Met Val Pro Ser Asp Pro Val Asp Gly Pro Tyr Gly Thr
                245                 250                 255

Gln Ile Tyr Asp Gln Val Val Ala Ser Ala Gly Cys Gly Ser Ala Ser
            260                 265                 270

Asp Lys Leu Ala Cys Leu Arg Ser Ile Ser Asn Asp Lys Leu Phe Gln
        275                 280                 285

Ala Thr Ser Asp Thr Pro Gly Ala Leu Ala Tyr Pro Ser Leu Arg Leu
    290                 295                 300

Ser Phe Leu Pro Arg Pro Asp Gly Thr Phe Ile Thr Asp Asp Met Phe
305                 310                 315                 320

Lys Leu Val Arg Asp Gly Lys Cys Ala Asn Val Pro Val Ile Ile Gly
                325                 330                 335

Asp Gln Asn Asp Glu Gly Thr Val Phe Ala Leu Ser Ser Leu Asn Val
            340                 345                 350

Thr Thr Asp Ala Gln Ala Arg Gln Tyr Phe Lys Glu Ser Phe Ile His
        355                 360                 365

Ala Ser Asp Ala Glu Ile Asp Thr Leu Met Ala Ala Tyr Pro Ser Asp
    370                 375                 380

Ile Thr Gln Gly Ser Pro Phe Asp Thr Gly Ile Phe Asn Ala Ile Thr
385                 390                 395                 400

Pro Gln Phe Lys Arg Ile Ala Ala Val Leu Gly Asp Leu Ala Phe Thr
                405                 410                 415

Leu Pro Arg Arg Tyr Phe Leu Asn His Phe Gln Gly Gly Thr Lys Tyr
            420                 425                 430

Ser Phe Leu Ser Lys Gln Leu Ser Gly Leu Pro Val Ile Gly Thr His
        435                 440                 445

His Ala Asn Asp Ile Val Trp Gln Asp Phe Leu Val Ser His Ser Ser
    450                 455                 460

Ala Val Tyr Asn Asn Ala Phe Ile Ala Phe Ala Asn Asp Leu Asp Pro
465                 470                 475                 480

Asn Lys Ala Gly Leu Leu Val Asn Trp Pro Lys Tyr Thr Ser Ser Ser
                485                 490                 495

Gln Ser Gly Asn Asn Leu Leu Gln Ile Asn Ala Leu Gly Leu Tyr Thr
            500                 505                 510

Gly Lys Asp Asn Phe Arg Thr Ala Gly Tyr Asp Ala Leu Phe Thr Asn
        515                 520                 525

Pro Ser Ser Phe Phe Val
    530

<210> SEQ ID NO 5
<211> LENGTH: 1605
<212> TYPE: DNA
<213> ORGANISM: Candida rugosa

<400> SEQUENCE: 5
gctcccactg ccacgctcgc caacggcgac accatcaccg gtctcaacgc catcatcaac    60
gaggcgttcc tcggcattcc ctttgccgag ccgccggtgg gcaacctccg cttcaaggac   120

```
cccgtgccgt actccggctc gctcgatggc cagaagttca cttcttacgg cccgtcttgc     180
atgcagcaga accccgaggg cacctacgag gagaacctcc ccaaggcagc gctcgacttg     240
gtgatgcagt ccaaggtgtt tgaggcggtg tctccgtcta gcgaggactg tctcaccatc     300
aacgtggtgc ggccgccggg caccaaggcg ggtgccaacc tcccggtgat gctctggatc     360
tttggcggcg ggtttgaggt gggtggcacc agcaccttcc ctcccgccca gatgatcacc     420
aagagcattg ccatgggcaa gcccatcatc cacgtgagcg tcaactaccg cgtgtcgtcg     480
tgggggttct tggctggcga cgagatcaag gccgagggca gtgccaacgc cggtttgaag     540
gaccagcgct tgggcatgca gtgggtggcg gacaacattg cggcgtttgg cggcgacccg     600
accaaggtga ccatctttgg cgagtctgcg ggcagcatgt cggtcatgtg ccacattctc     660
tggaacgacg gcgacaacac gtacaagggc aagccgctct ccgcgcgggg catcatgcag     720
tctggggcca tggtaccgtc ggacgcggtg gacggcattt acggcaacga gatctttgac     780
ctcttggcgt cgaacgcggg ctgcggcagc gccagcgaca gcttgcgtg cttgcgcggt     840 gtgtctagcg acacgttgga ggacgccacc aacaacaccc ctgggttctt ggcgtactcc     900
tcgttgcggt tgtcttatct cccgcggccc gacggcgtga acatcaccga cgacatgtat     960
gccttggtcc gcgagggcaa gtatgcaaac attcctgtga tcatcggcga ccagaacgac    1020
gagggcacct tctttggcac ctcttctttg aacgtgacca cggatgccca agcccgcgaa    1080
tacttcaagc agtcttttgt ccacgccagc gacgcggaga ttgacacgtt gatgacggcg    1140
taccccggtg acatcaccca gggttctccg ttcgacacgg gtattctcaa cgccctcacc    1200
ccgcagttca agagaatctc tgcggtgctc ggcgaccttg gtttcactct agcccgtcgc    1260
tacttcctca accactacac cggcggcacc aagtactcat tcctctctaa gcagctctct    1320
ggcttgccgg tgctcggaac gttccactcc aacgacattg tcttccagga ctacttgttg    1380
ggcagcggct cgctcatcta caacaacgcg ttcattgcgt ttgccacgga cttggacccc    1440
aacaccgcgg ggttgttggt gaagtggccc gagtacacca gcagctctca gtctggcaac    1500
aacttgatga tgatcaacgc cttgggcttg tacaccggca aggacaactt ccgcaccgcc    1560
ggctacgacg cgttgttctc caacccgccg tctttctttg tgtag                    1605

<210> SEQ ID NO 6
<211> LENGTH: 1605
<212> TYPE: DNA
<213> ORGANISM: Candida rugosa

<400> SEQUENCE: 6
gtacccaccg ccacgctcgc caacggcgac accatcaccg gtctcaacgc cattgtcaac      60
gaaaagtttc tcggcatacc gtttgccgag ccgcccgtgg gcagcctccg cttcaagccg     120
cccgtgccgt actcggcgtc gctcaacggc cagcagttta cctcttacgg cccgtcttgc     180
atgcagatga acctatgggg ctcgtttgag gacacacttc ccaagaatgc gcttgacttg     240
gtgctccagt ccaagatctt ccaagtggtg cttcccaacg acgaggactg tctcaccatc     300
aacgtgatcc ggccgccggg caccagggcc agtgctggtc tcccggtgat gctctggatc     360
tttggcggtg ggtttgagct tggcggctcc agcctcttcc aggagacca gatggtggcc     420 aagagcgtgc tcatgggtaa accggtgatc cacgtgagca tgaactaccg cgtggcgtca     480
tgggggttct tggccggccc cgacatccag aacgaaggca gcgggaacgc cggcttgcat     540
gaccagcgct tggccatgca gtgggtggcg gacaacattg ctgggtttgg cggcgacccg     600
agcaaggtga ccatatacgg cgagtctgcg ggcagcatgt cgacgtttgt gcaccttgtg     660
```

```
tggaacgacg gcgacaacac gtacaacggc aagccgttgt tccgcgccgc catcatgcag      720
tctggctgca tggtgccgtc tgaccggtg  acggcacgt  acggaccga  gatctacaac      780 caggtggtgg cgtctgccgg gtgtggcagt gccagcgaca agctcgcgtg cttgcgcggc      840
ctttctcagg acacgttgta ccaggccacg agcgacacgc cggcgtgtt  ggcgtacccg      900 tcgttgcggt tgtcttatct cccgcggccc gacggcacct tcatcaccga cgacatgtat     960
gccttggtgc gggacggcaa gtacgcacac gtgccggtga tcatcggcga ccagaacgac    1020
gagggcactt tgtttgggct ctcttctttg aacgtgacca cagatgctca ggcacgggcg    1080
tacttcaagc agtctttcat ccacgccagc gatgcggaga tcgacacgtt gatggcggcg    1140
tacaccagcg acatcaccca gggttctccg ttcgacaccg gcatcttcaa tgccatcacc    1200
ccgcagttca acggatctc  tgcgttgctt ggcgaccttg cgttcacgct tgcgcgtcgc    1260
tacttcctca actactacca gggcggcacc aagtactcgt tcctctctaa gcagctttct    1320
gggttgcccg tcttgggcac cttccacggc aacgacatca tctggcagga ctacttggtg    1380
ggcagcggca gtgtgatcta caacaacgcg ttcattgcgt ttgccaacga cctcgacccg    1440
aacaaggcgg gcttgtggac caactggccc acgtacacca gcagctctca gtctggcaac    1500
aacttgatgc agatcaacgg cttggggttg tacaccggca aggacaactt ccgcccggat    1560
gcgtacagcg ccctcttttc aacccgccg  tctttctttg tgtag                    1605

<210> SEQ ID NO 7
<211> LENGTH: 1605
<212> TYPE: DNA
<213> ORGANISM: Candida rugosa

<400> SEQUENCE: 7
gctcccaccg ccaagctcgc caacggcgac accatcaccg gtctcaacgc catcatcaac      60
gaggcgttcc tcggcattcc cttttgccgag ccgccggtgg gcaacctccg cttcaaggac     120
cctgtgccgt actctggctc gctcaacggc cagaagttca cttcttacgg cccgtcttgc     180
atgcagcaga  ccccgaggg  cacgtttgaa gagaaccttg gcaagacggc actcgacttg    240
gtgatgcagt ccaaggtgtt ccaggcgtg  cttcccaga  gtgaggactg cctcaccatc    300
aacgtggtgc ggccgccggg caccaaggcg ggcgccaacc tcccggtcat gctctggatc    360
tttggcggtg ggtttgagat cggcagcccc accatcttcc ctcccgccca gatggtcacc    420
aagagtgtgc tcatgggcaa gcacatcatc cacgtggccg tcaactaccg tgttgcctcg    480
tgggggttct tggctggtga tgacatcaag gccgagggca gcgggaacgc cggcttgaag    540
gaccagcgtt tgggcatgca gtgggtggca gacaacattg ccgggttcgg cggcgacccg    600
agcaaggtga ctatctttgg cgagtctgcg ggcagcatgt ccgtgttgtg ccacctcatc    660
tggaacgacg gcgacaacac gtacaagggc aagccgttgt tccgcgcggg catcatgcag    720
tctggagcca tggtgccgtc tgaccccggtg acggcacgt  acggcaacga gatctacgac    780 ctcttttgtct cgagtgctgg ctgtggcagc gccagcgaca agctcgcgtg cttgcgcagt    840
gcgtctagcg acaccttgct cgatgccacc aacaacactc ctgggttctt ggcgtactcc    900
tcgttgcggt tgtcttatct cccgcggccc gacggcaaga acatcaccga tgacatgtac    960
aagttggtgc gcgacggcaa gtatgcaagc gttcccgtga tcattggcga ccagaacgac   1020
gagggcacca tctttgggct ctcttctttg aacgtgacca cgaatgctca ggcccgtgct   1080
tacttcaagc agtctttcat ccacgccagc gacgcggaga tcgacacctt gatggcggcg   1140
```

```
taccccagg acatcaccca gggttctccg ttcgacacgg gtgttctcaa cgccctcacc    1200
ccgcagttca agagaatctc tgcggtgctc ggcgaccttg cattcatcca cgcccgccgc    1260
tacttcctca accacttcca gggcggcacc aagtactcgt tcctctctaa gcagctctct    1320
gggttgccaa tcatgggcac cttccatgcc aacgacattg tgtggcagga ctacttgttg    1380
ggaagcggca gcgtcatcta caacaacgcg tttatcgcgt tcgccaccga cttggacccc    1440
aacaccgcgg ggttgttggt gaactggccc aagtacacca gcagctctca gtctggcaac    1500
aacttgatga tgatcaacgc cttgggcttg tacaccggca aggacaactt ccgcaccgct    1560
ggctacgacg cgttgatgac caacccgtct tctttctttg tgtag                   1605
```

<210> SEQ ID NO 8
<211> LENGTH: 1605
<212> TYPE: DNA
<213> ORGANISM: Candida rugosa

<400> SEQUENCE: 8

```
gtacccactg ccacgctcgc caacggcgac accatcaccg gtctcaacgc catcatcaac     60
gaggcgttcc tcggtattcc ctttgctcag ccgccggtgg gcaacctccg cttcaagccg    120
cctgtgccgt actcggcgtc tctcaatggt cagaagttta cttcgtatgg cccttcgtgc    180
atgcagatga acccattggg caactgggac tcctcgcttc ccaaggctgc catcaactcc    240
ttgatgcagt ccaagctctt ccaggcgtg cttcctaacg gcgaggactg tctcaccatc    300
aacgtggtgc ggccgtcagg caccaagccg ggtgccaacc tccccgtgat ggtgtggatt    360
tttggcggcg gtttgaggt tggcggctcc agtctcttcc ctcccgcaca gatgatcacc    420
gccagcgtgc ttatgggcaa gcccatcatc cacgtgagca tgaactaccg cgttgcttcg    480 tggggggttct tggctggtcc agacatcaag gccgagggca gcgggaacgc cggttttgcac    540 gaccaacgct tgggtttgca gtgggtggcg gacaacattg ccggggttcgg cggcgacccg    600 tccaaggtga ccatctttgg tgagtcggcg gcagcatgt cggtaatgtg tcagctcctc    660
tggaacgacg gcgacaacac gtacaacggc aagccgttgt tccgtgccgc catcatgcag    720
tctggggcca tggtgccgtc ggacccgtg gatgggccct acggcacgca gatctacgac    780
caggtggttg cttcagccgg ctgtggcagt gccagcgaca agctcgcgtg cttgcgcagc    840
atctcgaacg acaaactctt ccaggccacc agcgacactc cggggggcctt ggcgtaccccc    900 tcgttgcggt tgtcgttttct cccgcggccc gacggcacct catcaccga tgacatgttc    960 aagttggtgc gcgacggcaa gtgtgccaac gttccggtga tcattggcga ccagaacgac    1020
gagggcacag tgtttgcgtt gtccagcttg aacgtgacta cggatgctca ggcacgccag    1080
tacttcaagg aaagcttcat ccacgccagc gacgcggaga tcgacacctt gatggcggcg    1140
taccccagcg acatcaccca gggtagtccg ttcgacaccg gcatcttcaa cgccatcacc    1200
ccgcagttca acggattgc agcggtgctt ggtgaccttg cgttcactct ccccggcgc    1260 tacttcctca accacttcca gggcggcacc aagtactcgt tcctctcgaa gcagcttagt    1320
gggttgccgg tgattggcac ccaccacgcc aacgacattg tgtggcagga cttttttggtg    1380 agccacagca gcgccgtgta caacaacgcg tttattgcct ttgccaacga cctcgacccg    1440
aacaaggccg gtttgcttgt gaactggccc aagtacacca gcagctctca gtcaggcaac    1500
aacttgttgc agatcaacgc cttgggcttg tacaccggca aggacaactt ccgcaccgct    1560
ggctacgacg cgttgtttac caacccgtcg tcgtttttttg tttag                   1605
```

METHODS FOR PRODUCING BIODIESEL BY RECOMBINANT LIPASE

CROSS-REFERENCE TO RELATED APPLICATIONS

This application claims the benefit of Taiwan Application No. 104137833 filed on Nov. 17, 2015, the entire disclosure of which is incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 21, 2016, is named 29218US-sequence listing-final-20160105.txt and is 54,776 bytes in size.

BACKGROUND OF THE INVENTION

Field of the Invention

The present disclosure relates to methods for producing biodiesel, and more particularly, to a method for producing biodiesel from non-edible oils.

Description of Related Art

Biodiesel is a re-generable fuel for replacing diesel. The molecules in biodiesel are primarily fatty acid methyl esters (FAMEs) usually obtained from trans-esterification of oils. Rapid alkali-catalyzed chemical processes with high yields are mainly used for the commercial productions of biodiesel. However, such processes are operated at high temperature and pressure, which are extremely energy consuming. The processes also have various drawbacks, such as saponification, difficulties in recycling the glycerol byproduct, the need to remove residual salts, and the productions of large amounts of effluent, which lead to environmental pollution. Therefore, as compared with the chemical processes for producing biodiesel, the processes for producing biodiesel by enzymatic catalysis under moderate conditions are regarded as environmentally friendly processes.

The conventional processes for producing biodiesel often require expensive refined oils as raw material, such as soybean oil, rapeseed oil, cottonseed oil and sunflower oil. The oil raw material for producing biodiesel takes up 85% or more of the production cost. These processes are extremely costly to the developing countries with shortage of such edible oil. Hence, the use of non-edible oil in the production of biodiesel contributes significantly to the economy and environmental protection.

Current researches have found that some enzymatically catalyzed processes in producing biodiesel can utilize low cost non-edible oil. For example, Abulla et al. (*Rev. Biotechnol.* 31, 53-64. 2011) and You et al. (*Bioresour. Technol.* 148, 202-207. 2013) found that various types of lipases from different bacterial strains can convert *Jatropha* oil into biodiesel. However, those researches all used immobilized lipases. Although the immobilization of enzymes improves the enzyme stability and leads to easy separation of products and repeated uses of enzymes, its expensive cost is unfavorable for industrial production.

*Candida rugosa* lipase (CRL) is a commercially available enzyme with an extremely wide range of applications. Various lipase isomers (i.e., isozymes) can be isolated from commercially available crude CRL. However, five *C. rugosa* genes encoding lipase with different expression levels have currently been identified, and the amino acid sequences encoding the five genes have high homology. As such, it is difficult to directly purify each of the isozymes from the *C. rugosa* culture in the industrial application scale. Moreover, *C. rugosa* translates its CTG codon into serine, such that the recombinant CRL isozymes expressed in a typical host cell (which translates the CTG codon into leucine) become non-functional.

In light of the drawbacks in the above conventional technologies, the present disclosure hereby provides a method for producing biodiesel with high yield using a recombinant yeast lipase to resolve the drawbacks.

SUMMARY OF THE INVENTION

The present disclosure provides a method for producing biodiesel, including:

providing recombinant *C. rugosa* lipase including a sequence having at least 90% of identity to one of SEQ ID NOs: 1 to 4 and the same activity with one of SEQ ID NOs: 1 to 4;

reacting the recombinant *C. rugosa* lipase with non-edible oil in the presence of a first alcoholic solution; and isolating the biodiesel from the reacted solution.

In one embodiment, the recombinant *C. rugosa* lipase is obtained by an expression in recombinant *Pichia pastoris*.

In one embodiment, the non-edible oil is at least one selected from the group consisting of *Jatropha* oil, Karanja oil and castor oil.

In one embodiment, in step (2), a dose of the recombinant *C. rugosa* lipase is from 40 U to 160 U per gram of non-edible oil. When the reaction starts, a molar concentration ratio of the non-edible oil and the first alcoholic solution is from 1:3 to 1:4.5.

In one embodiment, the reactants in step (2) comprise the recombinant *C. rugosa* lipase, the non-edible oil, the first alcoholic solution and water, and the water content is from 30 wt % to 50 wt %, based on a weight of the reactants.

In one embodiment, step (2) is performed at a temperature of from 10° C. to 37° C. and for a reaction time of from 4 to 72 hours.

In one embodiment, step (2) includes step (2') for adding a second alcoholic solution to the first alcoholic solution after the reaction starts, wherein the second alcoholic solution is added within 8 to 24 hours after the reaction starts. In another embodiment, the second alcoholic solution is the same as the first alcoholic solution. In another embodiment, the first alcoholic solution is methanol.

In one embodiment, the recombinant *C. rugosa* lipase is in liquid form. In another embodiment, the method further includes step (4) for recycling a residual solution containing the recombinant *C. rugosa* lipase after the biodiesel is isolated.

The present disclosure further provides a method for producing biodiesel, including:

providing a recombinant *C. rugosa* lipase including a sequence having at least 90% of identity to one of SEQ ID NOs: 1 to 4 and the same activity with one of SEQ ID NOs: 1 to 4;

reacting the recombinant *C. rugosa* lipase with a non-edible oil in the presence of a first alcoholic solution at a temperature of from 10° C. to 37° C., and when the reaction starts, a molar concentration ratio of the non-edible oil and the first alcoholic solution is from 1:3 to 1:4.5; and isolating the biodiesel from the reacted solution.

In one embodiment, reactants in step (2) comprise the recombinant *C. rugosa* lipase, the non-edible oil, the first alcoholic solution and water, and the water content is from 30 wt % to 50 wt %, based on a weight of the reactants.

In one embodiment, the recombinant *C. rugosa* lipase is obtained by an expression in recombinant *P. pastoris*, and the first alcoholic solution is methanol.

In one embodiment, step (2) includes step (2') for adding a second alcoholic solution to the first alcoholic solution after the reaction starts, wherein the second alcoholic solution is added within 8 to 24 hours after the reaction starts.

The method of the present disclosure can effectively use non-edible oil for trans-esterification. The method of the present disclosure can also use liquid CRL, such that the treatment step prior to the immobilization of enzymes is omitted and efficacy (particularly the recycling and reuse of liquid CRL) over the technology using immobilized enzymes is brought about, and thereby lowering the cost. Thus, the method of the present disclosure has the potential for industrial applications.

BRIEF DESCRIPTIONS OF THE DRAWINGS

Figure 4:
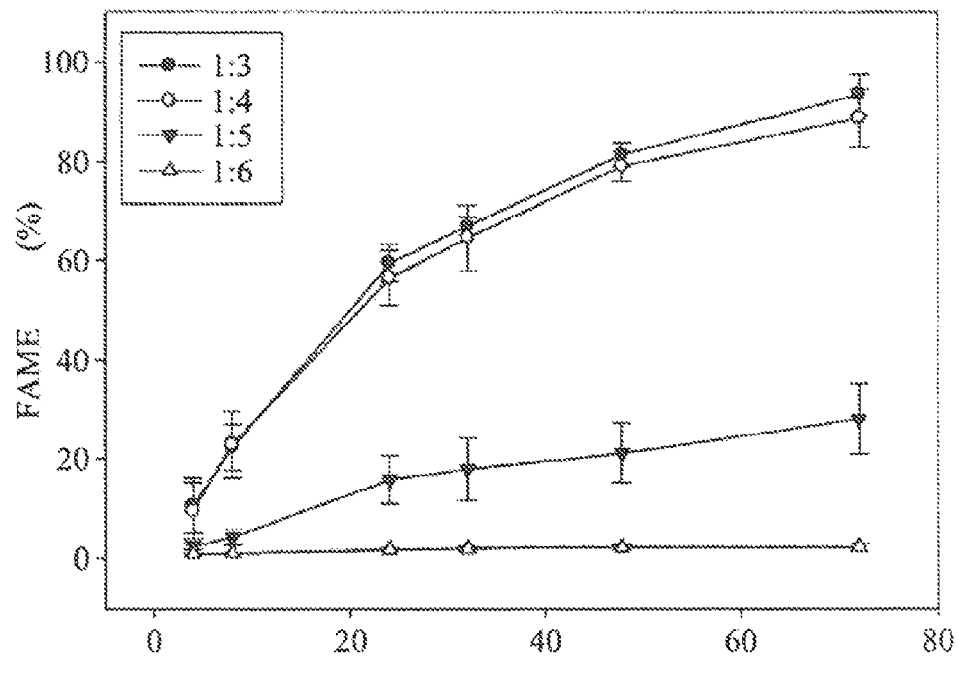
Figure 5A:
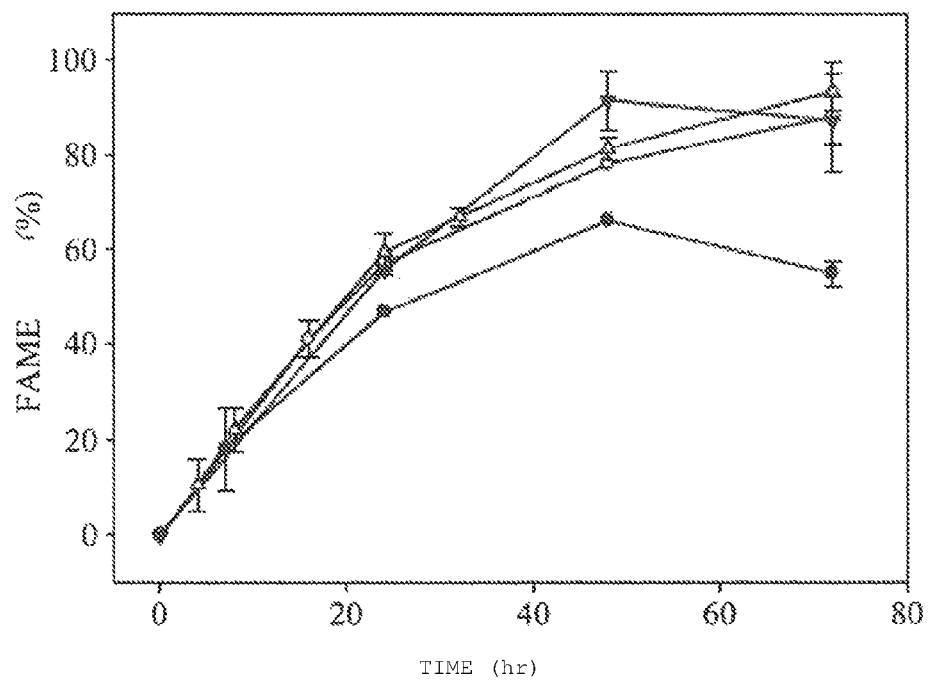
Figure 5B:
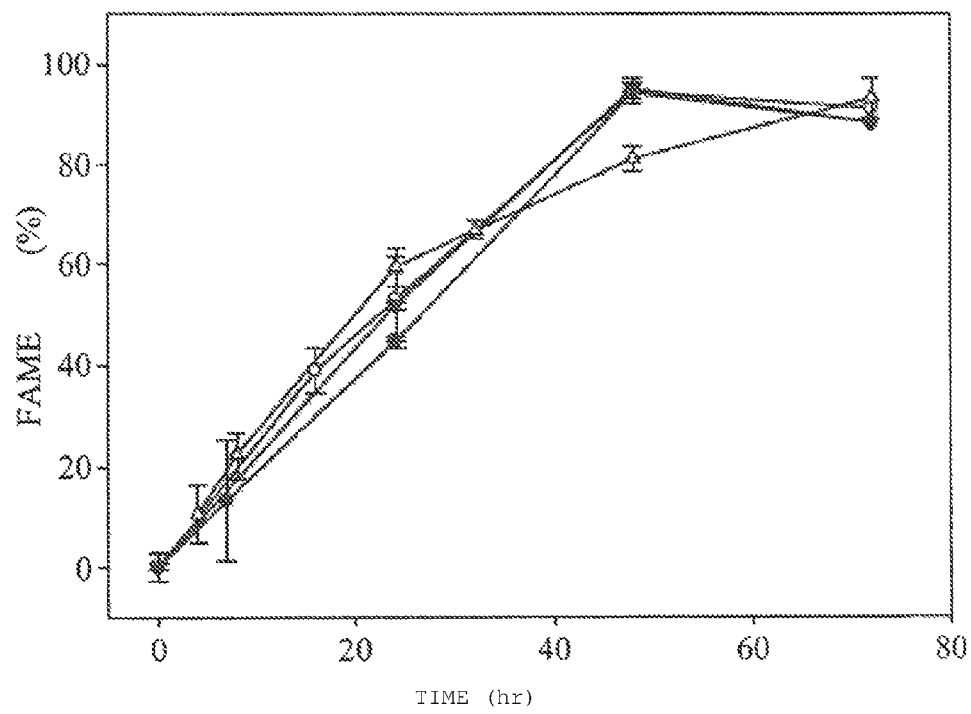

FIG. 4 shows the effects of molar concentrations of substrates on the yields of FAME at different time points, wherein the reaction conditions were a water content of 50%, a CLR2 dose of 160 U, 1 g of *Jatropha* oil, oil and methanol at ratios of molar concentrations of 1:3, 1:4, 1:5 and 1:6, a rotating speed of 250 rpm, 37° C., and 72 hours; and FIGS. 5A and 5B show the effects of different stepwise feeding approaches of methanol on the yields of FAME at different time points, wherein FIG. 5A shows the addition of 1 eq. of methanol at the beginning of the reaction, and the respective additions of 1 eq. of methanol at the $8^{th}$ hour (●), the $16^{th}$ hour (○), and the $24^{th}$ hour (▼), FIG. 5B shows the addition of 1 eq. of methanol at the beginning of the reaction, and the respective additions of 0.5 eq. of methanol at the $8^{th}$ hour (●), the $16^{th}$ hour (○), and the $24^{th}$ hour (▼), the symbol (Δ) indicates that no additional methanol was added during the reaction, and the reaction conditions were a water content of 50%, a CLR2 content of 80 U, 0.5 g of *Jatropha* oil, a rotating speed of 250 rpm, 37° C., and 72 hours.

DETAILED DESCRIPTION OF THE PREFERRED EMBODIMENTS

The present disclosure is described by using the following embodiments, so as to enable a person skilled in the art to conceive the other advantages and effects of the present disclosure from the disclosure of the present specification. However, the examples in the present disclosure are not used for limiting the scope of the present application. Any one skilled in the art can alter or modify the present disclosure in any way, without departing from the spirit and scope thereof. Therefore, the scope of the present disclosure should be accorded with the definitions in the appended claims.

It should be noted that the singular forms "one" and "the" used in the present specification include plural forms too, unless clearly and definitively limit to one specific form. Unless clearly indicated in the context, the terms "or" and "and/or" are used interchangeably. At the same time, the terms, such as "first" and "second," used in the present specification are merely for enhancing the understanding of the descriptions, rather than limit the implementable scope of the present disclosure. Without materially altering the technical content, the alteration or adjustment of relative relationships should also be regarded as fallen within the implementable scope of the present disclosure.

The present disclosure provides a method for producing biodiesel using a recombinant lipase expressed by a recombinant yeast.

As used herein, "lipase" (also referred to triglyceride hydrolase) is a type of hydrolase mainly responsible for hydrolyzing glyceride. Lipase is a necessary enzyme which hydrolyzes lipid (triglyceride) into glycerin and fatty acid in a natural environment. In the presence of a non-aqueous medium, a lipase can catalyze other synthetic reactions, including biotransformation of carboxyl groups, such as esterification, trans-esterfication, and the like. Trans-esterification refers to the process of producing another type of ester ($RCOOR_2$) by mixing and reacting an ester ($RCOOR_1$) and an alcohol ($R_2OH$) at a specific ratio.

As used herein, "*C. rugosa* lipases" refers to recombinant *C. rugosa* lipase isozymes, which include natural *C. rugosa* lipases and variants thereof (hereinafter referred to as recombinant *C. rugosa* lipases), e.g., amino acid sequences represented by SEQ ID NOs. 1 to 4. "Isozymes" refers to enzymes with different properties, but with the same catalytic reactions. The isozymes can be present in different tissues or organs of the same organism in different amounts, and vary from one another by the primary structure or quaternary structure or post-translational modification of the proteins. Cells can regulate the catalytic activities of the isozymes based on the specific intracellular physiological conditions.

1. The present disclosure provides a method for producing biodiesel, including (1) providing a recombinant *C. rugosa* lipase including a sequence having at least 90% of identity to one of SEQ ID NOs: 1 to 4 and the same activity with one of SEQ ID NOs: 1 to 4; (2) reacting the recombinant *C. rugosa* lipase with non-edible oil in the presence of a first alcoholic solution; and (3) isolating the biodiesel from the reacted solution.

The recombinant *C. rugosa* lipase used in the present disclosure can be obtained by encoding a mutated nucleic acid sequence, wherein the mutated nucleic acid sequence and the wild-type nucleic acid sequence encoding a *C. rugosa* lipase have at least 80% of identity. According to an embodiment of the present disclosure, the mutated nucleic acid sequence includes a sequence represented by at least one of SEQ ID NOs. 5 to 8. Alternatively, the mutated nucleic acid sequence includes a nucleic acid sequence of a polypeptide sequence having at least 90% (e.g., 95%, 98% or 100%) identity to an amino acid sequence represented by one of SEQ ID NOs. 1 to 4.

According to an embodiment of the present disclosure, the recombinant *C. rugosa* lipase used in the present disclosure can be recombinant CRL isozymes, CRL1, CRL2, CRL3 or CRL4, which respectively include amino acid sequences represented by SEQ ID NOs. 1 to 4, and can be respectively encoded by the sequences represented by SEQ ID NOs. 5 to 8, wherein SEQ ID NO.5 encoding CRL1 is a variant encoding the sequence (GenBank No. X64703) of wild-type *C. rugosa* lipase 1 (GenBank No. P20261); SEQ ID NO. 6 encoding CRL2 is a variant encoding the sequence (GenBank No. X64704) of wild-type *C. rugosa* lipase 2 (GenBank No. P32946); SEQ ID NO. 7 encoding CRL3 is a variant encoding the sequence (GenBank No. X66006) of wild-type *C. rugosa* lipase 3 (GenBank No. P32947); and SEQ ID NO. 8 encoding CRL4 is a variant encoding the sequence (GenBank No. X66007) of wild-type *C. rugosa* lipase 4 (GenBank No. P32948).

The recombinant *C. rugosa* lipase used in the present disclosure can be expressed by *P. pastoris*. *P. pastoris* is commonly used as the expression systems for expressing recombinant proteins, and has many advantages. For example, unlike prokaryotic cells which produce less active and insoluble inclusion bodies due to the inability to carry out post-translational modification, *P. pastoris* can perform post-translational modifications in eukaryotic cells, including protein folding, formation of disulfide bonds and glycosylation. *P. pastoris* has the feature of having high bacterial density. Researches showed that, in an appropriate fermentation environment, cellular density could be as high as 500 OD600 U/mL. Therefore, high-density fermentation for expressing a large amount of desirable proteins helps to lower the cost of industrial applications. Moreover, expression vectors can provide protein secretion signals to secrete recombinant proteins extracellularly. Furthermore, since *P. pastoris* itself secretes a small amount of endogenous proteins and no additional proteins are added in a culture, the purifying step is simple. As such, the loss of products during purification can be reduced.

As used herein, "recombinant *P. pastoris*" refers to *P. pastoris* expressing a recombinant *C. rugosa* lipase. According to an embodiment of the present disclosure, the recombinant *C. rugosa* lipase used in the present disclosure includes a sequence represented by at least one of SEQ ID NOs. 5 to 8, wherein SEQ ID NOs. 5 to 8 respectively encode the amino acid sequences represented by SEQ ID NOs. 1 to 4. Alternatively, *P. pastoris* used in the present disclosure includes a sequence having at least 90% of identity to one of SEQ ID NOs. 5 to 8, encoding a sequence having at least 90% of identity to and the same activity with one of SEQ ID NOs. 1 to 4. Preferably, *P. pastoris* includes a sequence of at least one of SEQ ID NOs. 6 to 8. More preferably, *P. pastoris* includes a sequence of at least one of SEQ ID NOs. 6 to 8.

According to an embodiment of the present disclosure, the oil raw materials for producing biodiesel of the present disclosure include, but not limited to, edible oils (such as soybean oil, rapeseed oil, cottonseed oil and sunflower oil), non-edible oils (such as *Jatropha* oil, Karanja oil and castor oil), and slop oil. Preferably, *Jatropha* oil is used as the oil raw material for producing biodiesel of the present disclosure.

According to an embodiment of the present disclosure, the first alcoholic solution used in the present disclosure includes, but not limited to, methanol, ethanol, propanol, isopropanol and butanol. Preferably, methanol is used in the present disclosure as the first alcoholic solution in reactants. According to a preferred embodiment of the present disclosure, when the first alcoholic solution is methanol, the biodiesel produced by the present invention is fatty acid methyl ester.

According to an embodiment of the present disclosure, the dose of recombinant CRL for performing transesterification in step (2) can be from 40 U to 160 U per gram of oil raw material. For example, when 0.5 g of oil raw material is used, the dose of the recombinant CRL can be in the range of from 20 U to 80 U. When 1 g of oil raw material is used, the dose of the recombinant CRL can be in the range of from 40 U to 160 U. Preferably, the dose of recombinant CRL is 160 U per gram of oil raw material.

According to an embodiment of the present disclosure, the reactants in trans-esterification include the recombinant *C. rugosa* lipase, the non-edible oil, the first alcoholic solution and water. Moreover, the water content is at least 30 wt %, preferably at least 40 wt %, and more preferably at least 50 wt %, based on the weight of the reactants.

According to an embodiment of the present disclosure, trans-esterification is performed at 10° C. or at a higher temperature, preferably from 10° C. to 37° C., and more preferably at 37° C. According to an embodiment of the present disclosure, trans-esterification takes place for at least 4 hours, preferably from 4 to 72 hours, more preferably from 24 to 72 hours, and even more preferably from 48 to 72 hours.

According to an embodiment of the present disclosure, the molar concentration ratio of the oil raw material to the alcoholic solution for trans-esterification can be from 1:3 to 1:4.5, i.e., the alcoholic solution used can be from 1 eq. to 1.5 eq.

According to an embodiment of the present disclosure, step (2) of the present disclosure further includes step (2') for adding a second alcoholic solution to the first alcoholic solution after the reaction starts. According to an embodiment of the present disclosure, the second alcoholic solution includes, but not limited to, methanol, ethanol, propanol, isopropanol and butanol. Preferably, the second alcoholic solution is the same as the first alcoholic solution.

According to an embodiment of the present disclosure, 0.5 eq. to 1 eq. of the second alcoholic solution can be added within 8 to 24 hours after the reaction starts. For example, 0.5 eq. of second alcoholic solution can be added to the reactants within 8 to 24 hours after the reaction starts, and 1 eq. of second alcoholic solution can be added to the reactants within 16 to 24 hours after the reaction starts.

According to an embodiment of the present disclosure, after the addition of the second alcoholic solution, the molar concentration ratio of the oil raw material to the alcoholic solutions (first and second alcoholic solutions) is from 1:3 to 1:4.5. Preferably, in the method of the present disclosure, 1 eq. of the first alcoholic solution is included in the reactants when the reaction starts, and 0.5 eq. of the second alcoholic solution is included in the reactants after the reaction starts for 24 hours (wherein the molar concentration ratio of the oil raw material to the alcoholic solutions is smaller than or equal to 1:4.5).

According to an embodiment of the present disclosure, the recombinant CRL used in the present disclosure can be in liquid form. Moreover, the method of the present disclosure further includes step (4) for recycling the residual solution containing the recombinant CRL after isolating the biodiesel, wherein the residual solution includes the recombinant CRL. According to an embodiment of the present disclosure, the recycled residual solution can be added to an oil raw material, for direct use as a reactant for trans-esterification.

The effects of the present disclosure are further illustrated by the following specific embodiments, which are not intended to limit the scope of the present disclosure.

EXAMPLES

Example 1: Preparations of Oil Products

*Jatropha* seeds were obtained from Bioptik Biotechnology Inc. (Taiwan) and Shanhai Pass Horse Club (Taiwan). Karanja seeds and castor seeds were respectively collected from the Northern and Southern Taiwan. Crude oil products were obtained in accordance with hexane extraction in a Soxhlet device as described in Oliveria et al. (Biomass Bioenergy 33, 449-453, 2009). Standard fatty acid esters were purchased from Sigma Chemical Co. (St. Luis, Mo., USA).

Example 2: Preparations of Yeast Strains and Lipases

Four types of recombinant *P. pastoris* strains carrying the expression vectors of recombinant CRL isozymes, CRL1, CRL2, CRL3 and CRL4, respectively, were constructed by the methods described by Chang et al. (J. Agric. Food Chem. 54, 815-822. 2006; J. Agric. Food Chem. 54, 5831-5838. 2006), Lee et al. (Biochem. J. 366, 603-611. 2002), and Tang et al. (Arch. Biochem. Biophys. 387, 93-98. 2001). The amino acid sequences of CRL1, CRL2, CRL3 and CRL4 were represented by SEQ ID NOs. 1, 2, 3 and 4, respectively, and encoded by the nucleic acid sequences represented by SEQ ID NOs. 5, 6, 7 and 8, respectively.

The constructed recombinant *P. pastoris* strains were each incubated in a shaking bottle containing 50 mL of glycerin medium (2% of glycerin, 1% of yeast extract, and 0.5% of ammonium sulfate) and 100 µg/ml of zeocin, and incubated at 20° C. and a rotating speed of 200 rpm for 5 days. Afterwards, the culture was centrifuged at 7000×g for 10 minutes to collect fermented supernatant containing CRL. Then, the fermented supernatant was concentrated using Amicon Ultra-4 10 kDa cut off centrifugal filter (Merk KGaA, Darmstadt, Germany), such that a CRL enzyme solution was obtained.

Example 3: Enzyme Test

The activity of each of the lipases was determined using a spectrophotometer (Multiskan FC Microplate Photometer, Thermo Scientific) and using p-nitrophenylbutyrate as a substrate. The reactants for the determination contained 10 µL of the enzyme solution to be tested for, 10 µL of 20 mM phosphate buffer (pH 7.0), 0.25% of Triton X-100 and 0.5 mM of the substrate. The reaction was performed at 37° C. The increased absorbance due to the generation of the enzymatically hydrolyzed product, p-nitrophenol, at 405 nm within 10 minutes was measured and recorded, so as to calculate the initial rate of the lipase. One unit (U) of activity is defined as the amount of enzyme needed for the release of 1 micromole (µmol) of p-nitrophenol per minute under standard conditions.

The activities of the CRL1 to CRL4 enzyme solutions obtained in example 2 were 2857 U/mL, 674 U/mL, 307 U/mL and 586 U/mL, respectively.

Example 4: Syntheses of Enzymatically Catalyzed-Fatty Acid Methyl Esters

In the example, enzymatically catalyzed trans-esterification was used to generate FAME. Trans-esterification was conducted in a 20 mL screw-capped-bottle on a shaking incubator at 250 rpm.

Firstly, 0.5 g of a crude oil product was mixed with 1 equivalent of methanol (1 equivalent=3 moles of methanol/a mole of glycerides) in a reaction container. Then, each of the lipase solutions and de-mineralized water were mixed, and added to the reaction container based on the weight percentages of the masses of the oil used. Therefore, each of the lipase solutions also contained water, e.g., 50 µL of lipase solution provided 50 mg of water. The reaction mixture was incubated at 37° C. for 24 hours.

Example 5: Analysis on Yields

In the example, an analysis on the initial rates and yields was conducted on the products synthesized in enzymatically catalyzed trans-esterification. The analysis included the following steps of: reacting each of the enzymes and the crude oil products according to the method described in example 4, collecting products from the reaction mixture at predetermined time points, and performing a FAME test by gas chromatography.

Firstly, the reaction mixture was centrifuged at 8000×g for one minute, and the supernatant containing FAME was placed in a clean bottle for further analysis. Ten milligrams of the product to be tested for was added into 600 µL of methyl heptadecanoate (1 mg/mL, in n-hexane) as an internal standard for a quantitative analysis. Quantification of the FAME content was performed based on the European Standard Method, EN 14103. An FAME analysis was performed using Thermo TRACE™ 1300 gas chromatography equipped with a flame ionization detector, a programmable temperature vaporizing injector, and a TR-BioDiesel (F) column (30 m×0.25 mm; membrane thickness: 0.25 µm). One microliter of the product to be tested for was injected into the column by using a split mode (splitting rate of 1:100). Highly pure nitrogen gas was used as a carrier gas, and the flow rate was 1 mL/min. The temperature of the oven increased from 200° C. to 220° C. at a rate of 2° C./min and maintained at 260° C. for 10 minutes. The temperatures of the injector and detector were set at 260° C. and 270° C., respectively.

Example 6: Effects of CRL Isozymes on the Conversion of Non-Edible Oils

Four recombinant enzymes (CRL1 to CRL4) were expressed in recombinant *P. pastoris* according to the methods described in examples 1 to 5, and the fermented supernatants were collected. Then, the catalytic reactions of CRL in converting *Jatropha* oil, Karanja oil and castor oil into FAMEs were determined. The reactants for synthesizing FAME included 0.5 g of the oil product to be tested for, 1 eq. of methanol, 30% of water, and 40 U of the enzyme to be tested for, and the reaction conditions were 250 rpm, 37° C. and 24 hours.

The results are shown in TABLE 1, in which all of the recombinant CRL isozymes could catalyze the conversion of non-edible oils into FAME, wherein the catalytic efficiency of each of the recombinant CRL isozymes utilizing *Jatropha* oil was better than the catalytic efficiency of each of the recombinant isozymes utilizing Karanja oil or castor oil. The yield of the FAME (36.01%±2.50) obtained after the catalysis of *Jatropha* oil by CRL2 was comparable to the yield of the FAME (36.90%±0.30) obtained after being catalyzed by CRL4, but higher than the yield of FAME (17.31%±1.67) obtained after being catalyzed by CRL1 or the yield of FAME (24.26%±0.92) obtained after being catalyzed by CRL3. As shown from these results, CRL2 and CRL4 were the better isozymes for producing biodiesel from *Jatropha* oil.

TABLE 1

Comparison of the activity of CRL isozymes on trans-esterification of the three types of non-edible oil

| | Yield of FAME (%) | | |
|---|---|---|---|
| | Jatropha oil | Cantor oil | Karanja oil |
| CRL1 | 17.31% ± 1.67 | 2.30% ± 0.07 | 1.51% ± 0.11 |
| CRL2 | 36.01% ± 2.50 | 1.42% ± 0.04 | 1.47% ± 0.04 |
| CRL3 | 24.26% ± 0.92 | 0.68% ± 0.02 | 19.08% ± 0.29 |
| CRL4 | 36.90% ± 0.30 | 0.28% ± 0.14 | 0.22% ± 0.10 |

The fatty acids in *Jatropha* oil included 14.6% of palmitic acid (16:0), 6.9% of stearic acid (18:0), 46.2% of oleic acid (18:1) and 30.8% of linoleic acid (18:2). It is clear that long-chain fatty acids took up a larger portion in *Jatropha* oil, indicating that CRL2 and CRL4 were suitable for trans-esterification of long-chain fatty acids.

Shah and Gupta's research (Process Biochem. 42, 409-414. 2007) has pointed out that commercial CRLs could not effectively catalyze the production of FAME from *Jatropha* oil. However, it is found in the examples in the present specification that the recombinant CRL isozymes have specificity, i.e., different CRL isozymes utilize different substrates. Since the commercial CRLs lack the recombinant CRLs used in the present application, particularly, CRL2 and CRL4, the activity for catalyzing *Jatropha* oil is not found. Hence, as compared with conventional technologies, the method using specific CRL isozymes provided by the present invention can effectively produce biodiesel from *Jatropha* oil.

Example 7: Effects of Water Contents and Doses of Enzymes

In trans-esterification, water is essential for maintaining the configuration of enzymes, so as to increase the available interfacial surface area between water and oil. However, an excessive amount of water may dilute the amount of available methanol, and reverses trans-esterification into hydrolysis. In the present example, the optimal water contents and doses of enzymes for enzymatically catalyzing the synthesis of biodiesel were determined. According to the method described in example 4, the reaction for synthesizing FAME was carried out, and the water contents or doses of enzymes were adjusted.

Figure 1:
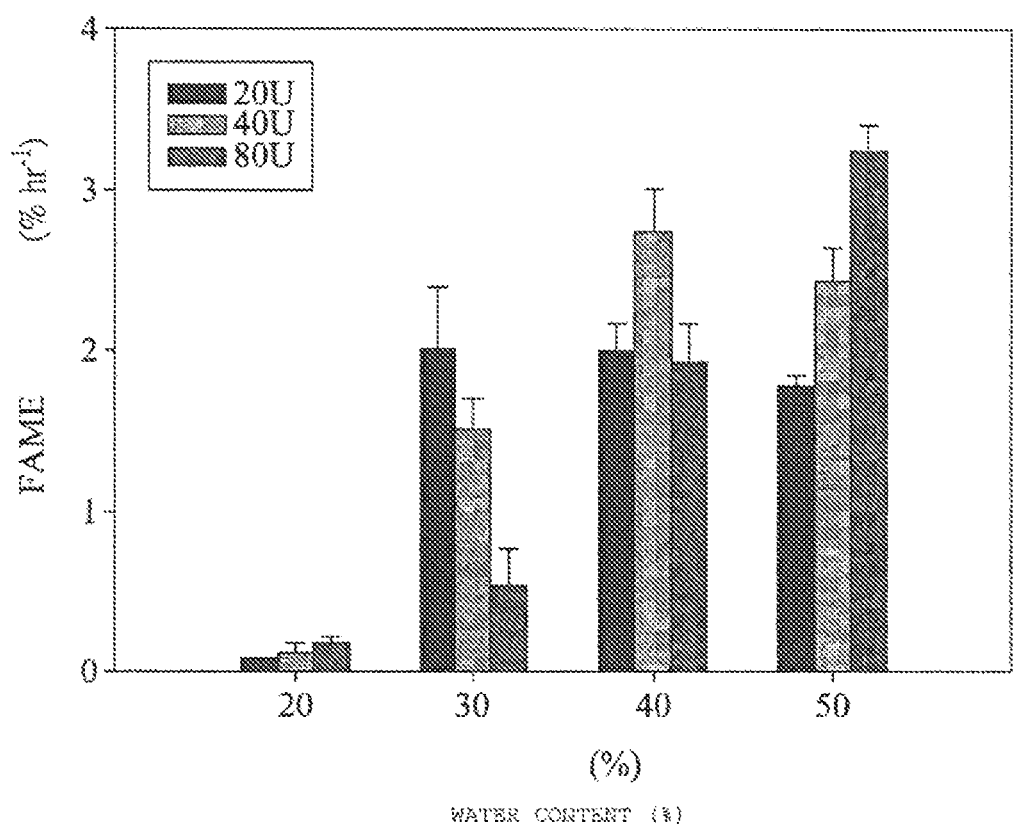
FIG. 1 shows the effects of water contents and CRL2 doses on the initial rates in the productions of FAME, wherein the reaction conditions were water contents of 20%, 30%, 40% and 50%, and CLR2 doses of 20U, 40U, and 80U, 0.5 g of *Jatropha* oil, 1 eq. of methanol, a rotating speed of 250 rpm, 37° C., and 4 hours.

FIG. 1 shows the effects of different water contents and different doses of CRL2 (20U, 40U and 80U, per 0.5 g of an oil product) on the initial rates and yields of FAME. It is clear from the results that any doses of CRL2 could not effectively catalyze a reaction when the water content was 20%. When the water content was 30%, a sufficient interfacial surface area was provided for 20U of CRL2. However, since the enzymes were diluted, the increases in water contents did not significantly affect the initial rates. A similar observation was made on the group containing a water content of 40% and 40 U of CRL2. The group containing 80 U of CRL2 and a water content of 50% could reach the maximum initial rate (3.25% $h^{-1}$).

Figure 2A:
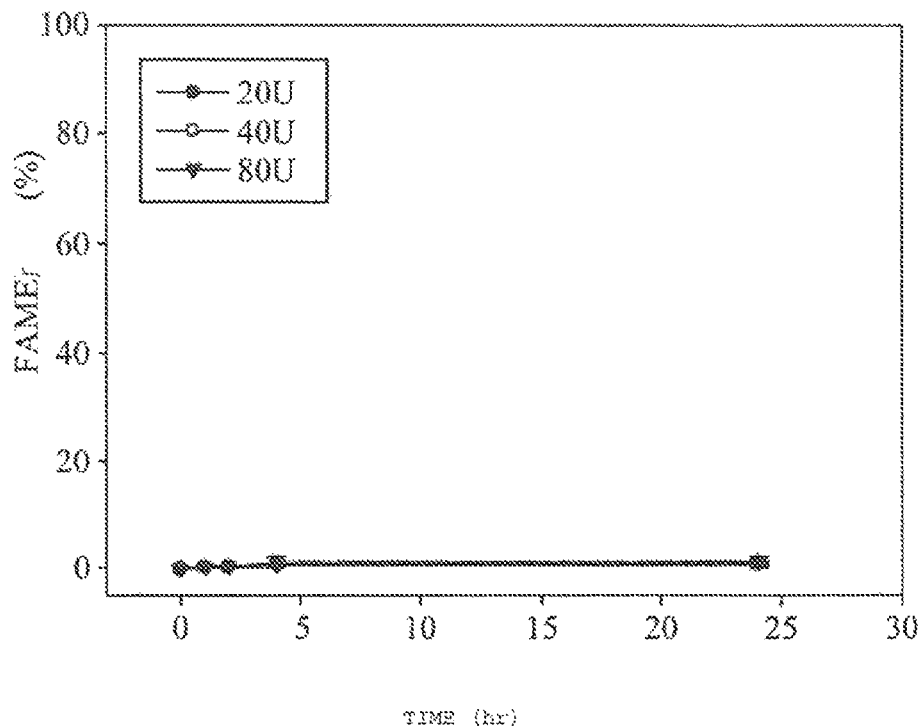
FIGS. 2A to 2D show the effects of water contents and CRL2 doses on the yields of FAME at different time points, wherein the reaction conditions were water contents of 20% (A), 30% (B), 40% (C) and 50% (D), and CLR2 doses of 20U, 40U, and 80U, 0.5 g of *Jatropha* oil, 1 eq. of methanol, a rotating speed of 250 rpm, 37° C., and 24 hours.
Figure 2B:
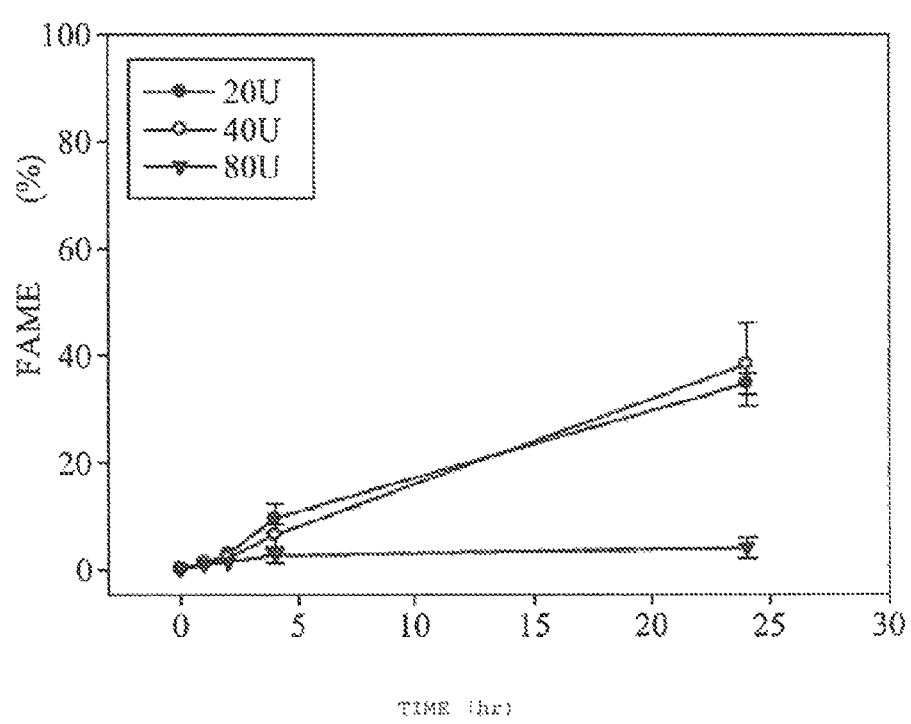
Figure 2C:
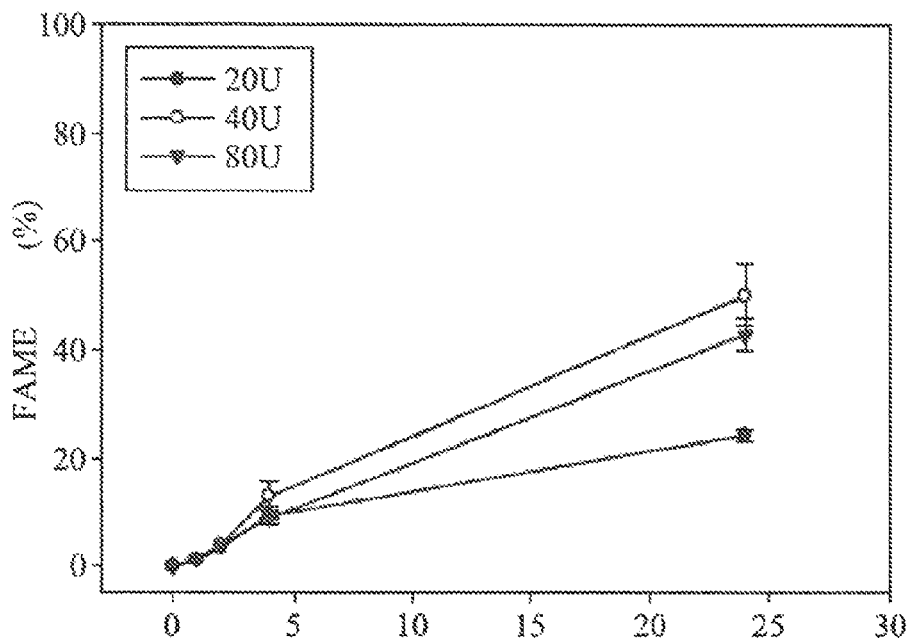
Figure 2D:
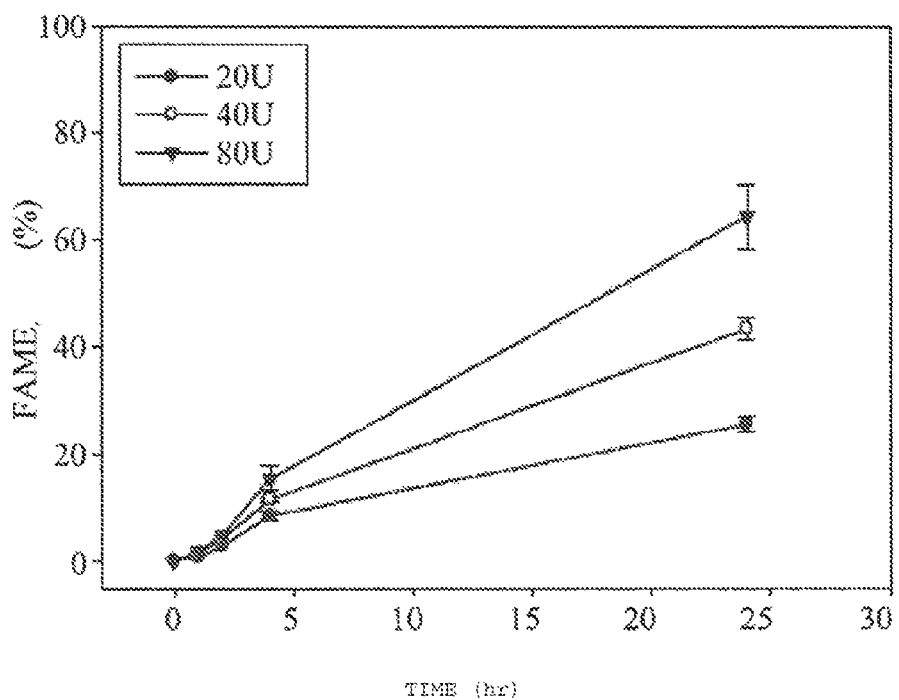

Moreover, FIG. 2A also shows that no FAME was produced, when the water content was 20%. Furthermore, as shown in FIGS. 2B to 2D, 24 hours after the reaction has started, the yield of FAME in the group containing 20U of CRL2 and a water content of 30% was 34%, which was better than the group containing 20U of CRL2 and a water content of 40% or 50%. The yield of FAME of the group containing 40U of CRL2 and a water content of 40% was 49.1%, which was better than the group containing 40U of CRL2 and a water content of 50%. The yield of FAME in the group containing 80U of CRL2 increased with an increasing amount of water content. When the water content was 50%, the yield reached a maximum of 62.9%. It appears that the ability of producing FAME by different doses of enzymes is strongly affected by the water contents.

Example 8: Effects of Temperatures

In the present example, the optimal temperatures for synthesizing the enzymatically catalyzed-biodiesel were determined. According to the method described in example 4, FAME was synthesized, and the reaction temperatures were adjusted, wherein the reaction mixture includes 0.5 g of *Jatropha* oil, 66 mg of methanol (the molar concentration ratio of oil to methanol was 1:3), 50% of water and 80 U of CRL2.

Figure 3:
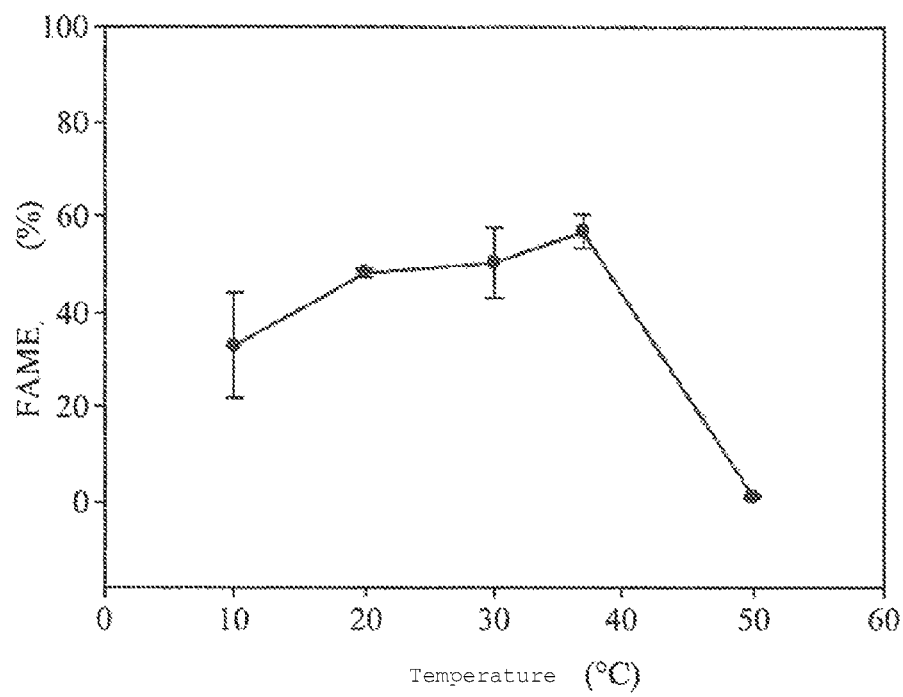
FIG. 3 shows the effects of reaction temperatures on the yields of FAME, wherein the reaction conditions were a water content of 50%, a CRL2 dose of 80 U, 0.5 g of *Jatropha* oil, 1 eq. of methanol, a rotating speed of 250 rpm, 10-50° C., and 24 hours.

As shown in FIG. 3, the yield of FAME increased with the increasing temperature in the range of from 10° C. to 37° C., and reached a maximum yield of 56.9% at 37° C. However, the yield of FAME decreased rapidly at 50° C. When the reaction temperatures were 10° C., 20° C. and 30° C., the activities of CRL2 were 57.7%, 84.8% and 88.4% at 37° C., respectively.

As compared with previous researches, Chang et al. (Food Chem. 155, 140-145. 2014) pointed out that the maximum yield of FAME obtained at 40° C. was only 40.2%, when using CRL2 to catalyze soybean oil to produce biodiesel. It is clear that as compared to refined edible oils, the method of using a non-edible oil provided by the present disclosure is more effectively in producing biodiesel and uses moderate reaction temperatures, such that it is suitable for industrial applications.

Example 9: Effect of Molar Concentration Ratios of Substrates

The complete conversion of triglyceride into FAME often required 1 stoichiometry (1 eq.) of methanol. Generally speaking, the more the alcohol being added, the higher trans-esterification yield increased. However, an excessive amount of alcohol also inhibits enzymatic activity, such that the yield of biodiesel is reduced.

In the present example, the most optimal molar concentrations of substrates for synthesizing enzymatically catalyzed-biodiesel were determined. According to the method described in example 4, FAME was synthesized, and the substrate concentrations (oil:methanol=1:3 to 1:6, i.e., 1 eq. to 2 eq. of methanol) were adjusted, wherein the reaction mixture included 50% of water and 80 U of CRL2 (per 0.5 g of *Jatropha* oil), and the reaction conditions were 37° C. and 72 hours.

As shown in FIG. 4, higher yields of FAME (93.5% and 88.8%) were reached, when the molar concentration ratios of oil to methanol were 1:3 and 1:4; and the yield of FAME decreased when the molar concentration ratio was 1:5 or 1:6. When the ratio of molar concentrations was 1:5 or 1:6, the amounts of methanol were 23.0% and 26.4% (w/w) (in an aqueous phase). The results show that the higher the amount of methanol in water, the lower the yield of FAME due to deactivation of CRL2.

Example 10: Effects of the Feeding Approaches of Methanol

In order to avoid deactivation of enzymes by methanol, methanol was gradually added with time to determine the effects of the feeding approaches of methanol on the yields of FAME.

According to the method described in example 4, FAME was synthesized, wherein 1 eq. of methanol was firstly added to the reactants when the reaction started, and then 1 eq. or 0.5 eq. of methanol was added at different time points (e.g., the $8^{th}$, $16^{th}$ or $24^{th}$ hour), i.e., a total of 1.5 eq. to 2 eq. of methanol was added in the reaction. As shown in the results in FIG. 5A, the additional addition of 1 eq. of methanol at the $8^{th}$ hour caused the deactivation of CRL2, and lowered the yield of FAME. The yield obtained after the additional addition of 1 eq. of methanol at the $16^{th}$ or $24^{th}$ hour was comparable to the yield achieved at the $72^{th}$ hour in the group without the additional addition of methanol. The yield achieved in the group with the additional addition of 1 eq. of methanol at the $24^{th}$ hour reached 91.6% at the $48^{th}$ hour. Based on a conversion rate of 60% at the $24^{th}$ hour, the total amount of methanol in the reactants did not exceed 1.4 eq. (i.e., oil:methanol=1:4.2). Therefore, the ratio of the molar concentrations of the substrates during the additional addition of 1 eq. of methanol at the $24^{th}$ hour did not cause deactivation of CRL2.

As shown in FIG. 5B, when additionally added 0.5 eq. of methanol at the $8^{th}$, $16^{th}$ and $24^{th}$ hour, the yields of FAME at the $48^{th}$ hour could reach 94.5%, 94.8% and 95.3%, respectively, which were all higher than the group without the additional addition of methanol.

It is clear from the above results that the most optimal feeding approach of methanol is the addition of 1 eq. of methanol when the reaction starts, and then adds 0.5 eq. of methanol at the $24^{th}$ hour without inhibiting CRL2. The results also show that the method provided by the present disclosure could achieve the comparable yield of FAME as the conventional technologies using immobilized enzymes, but at a reduced cost.

Example 11: Repeated Uses of Lipases

After batch-type trans-esterification was completed, the reaction mixture was centrifuged into three phases, wherein the upper layer was an FAME phase (which included FAME and residual glycerides), and the intermediate and lower layers were collectively called glycerin-aqueous phase (which included water, the generated glycerin, the used CRL and the residual methanol). The glycerin-aqueous phase could be recycled for the use in the next batch. When the glycerin-aqueous phase was repeatedly used, the residual methanol (about 0.5 eq.) could be regarded as the added methanol in the next batch. In the $2^{nd}$ to $4^{th}$ repeated batches, each of the feeding amounts of the initial methanol did not exceed 0.5 eq., such that the total amount of methanol was limited to 1 eq. or less. 0.5 eq. of methanol was additionally added at the $24^{th}$ hour, and the total reaction time was 48 hours. The yields of FAME obtained after the $1^{st}$, $2^{nd}$ and $3^{rd}$ repeated uses were 94.9%, 81.1% and 53%, respectively. Moreover, after the repeated uses on the $6^{th}$ day and the $3^{rd}$ use, 56% of the activity of the liquid CRL2 remained; and after the repeated uses on the $8^{th}$ day and the $4^{th}$ use, 37.5% of the activity remained.

From the above, the present invention identifies CRL isozymes for effective conversion of non-edible oil into biodiesel, increases the expression levels of CRL isozymes using a recombinant yeast expression system, and allows easy separation for recycling and repeated uses by performing trans-esterification using CRL isozymes in liquid form. Hence, the method of the present disclosure can significantly reduce the treatment procedure, lower the production cost, and effectively increase the purity of the final products. Moreover, the method of the present disclosure does not require the use of strong acidic and basic chemical substances, such that environmental pollution is avoided and the method is applicable under moderate conditions. Hence, the method is suitable for industrial productions.

The principles and effects of the present invention have been described using the above examples, which are not used to limit the present invention. Without departing from the spirit and scope of the present invention, any one skilled in the art can modify the above examples. Therefore, the scope of the present invention should be accorded with the claims appended.

The literatures cited by the present application are listed below, and each of the references is incorporated herein by reference.

1. Abdulla, R., Chan, E. S., Ravindra, P. 2011. Biodiesel production from *Jatropha curcas*: a critical review. Crit Rev Biotechnol, 31, 53-64.
2. Chang, S. W., Huang, M., Hsieh, Y. H., Luo, Y. T., Wu, T. T., Tsai, C. W., Chen, C. S., Shaw, J. F. 2014. Simultaneous production of fatty acid methyl esters and diglycerides by four recombinant *Candida rugosa* lipase's isozymes. Food Chem, 155, 140-5.
3. Chang, S. W., Lee, G. C., Shaw, J. F. 2006a. Codon optimization of *Candida rugosa* lip1 gene for improving expression in *Pichia pastoris* and biochemical characterization of the purified recombinant LIP1 lipase. J Agric Food Chem, 54, 815-22.
4. Chang, S W, Lee, G. C., Shaw, J. F. 2006b. Efficient production of active recombinant *Candida rugosa* LIPS lipase in *Pichia pastoris* and biochemical characterization of the purified enzyme. J Agric Food Chem, 54, 5831-8.
5. Chang, S. W., Li, C. F., Lee, G. C., Yeh, T, Shaw, J. F. 2011. Engineering the expression and biochemical characteristics of recombinant *Candida rugosa* LIP2 lipase by removing the additional N-terminal peptide and regional codon optimization. J Agric Food Chem, 59, 6710-9.
6. de Oliveira, J. S., Leite, P. M., de Souza, L. B., Mello, V. M., Silva, E. C., Rubim, J. C., Meneghetti, S. M. P., Suarez, P. A. Z. 2009. Characteristics and composition of *Jatropha gossypiifolia* and *Jatropha curcas* L. oils and application for biodiesel production. Biomass and Bioenergy, 33, 449-453.
7. Hama, S., Kondo, A. 2013. Enzymatic biodiesel production: an overview of potential feedstocks and process development. Bioresour Technol, 135, 386-95.
8. Kawakami, K., Oda, Y, Takahashi, R. 2011. Application of a *Burkholderia cepacia* lipase-immobilized silica monolith to batch and continuous biodiesel production with a stoichiometric mixture of methanol and crude *Jatropha* oil. Biotechnol Biofuels, 4, 42.
9. Lee, G. C., Lee, L. C., Sava, V, Shaw, J. F. 2002. Multiple mutagenesis of non-universal serine codons of the *Candida rugosa* LIP2 gene and biochemical characterization of purified recombinant LIP2 lipase overexpressed in *Pichia pastoris*. Biochem J, 366, 603-11.
10. Longhi, S., Fusetti, F, Grandori, R., Lotti, M., Vanoni, M., Alberghina, L. 1992. Cloning and nucleotide sequences of two lipase genes from *Candida cylindracea*. Biochim Biophys Acta, 1131, 227-32.

11. Lotti, M., Grandori, R., Fusetti, F, Longhi, S., Brocca, S., Tramontano, A., Alberghina, L. 1993. Cloning and analysis of *Candida cylindracea* lipase sequences. Gene, 124, 45-55.
12. Moser, B. R. 2008. Influence of Blending Canola, Palm, Soybean, and Sunflower Oil Methyl Esters on Fuel Properties of Biodiesel. Energy Fuels, 22, 4301-4306.
13. Park, E. Y., Sato, M., Kojima, S. 2008. Lipase-catalyzed biodiesel production from waste activated bleaching earth as raw material in a pilot plant. Bioresour Technol, 99, 3130-5.
14. Ranganathan, S. V., Narasimhan, S. L., Muthukumar, K. 2008. An overview of enzymatic production of biodiesel. Bioresour Technol, 99, 3975-81.
15. Shah, S., Gupta, M. N. 2007. Lipase catalyzed preparation of biodiesel from *Jatropha* oil in a solvent free system. Process Biochem, 42, 409-414.
16. Tang, S. J., Shaw, J. E, Sun, K. H., Sun, G. H., Chang, T. Y., Lin, C. K., Lo, Y. C., Lee, G. C. 2001. Recombinant expression and characterization of the *Candida rugosa* lip4 lipase in *Pichia* pastoris: comparison of glycosylation, activity, and stability. Arch Biochem Biophys, 387, 93-8.
17. Wang, Y., Liu, J., Gerken, H., Zhang, C., Hu, Q., Li, Y. 2014. Highly-efficient enzymatic conversion of crude algal oils into biodiesel. Bioresour Technol, 172, 143-9.
18. You, Q., Yin, X., Zhao, Y, Zhang, Y. 2013. Biodiesel production from *Jatropha* oil catalyzed by immobilized *Burkholderia cepacia* lipase on modified attapulgite. Bioresour Technol, 148, 202-7.

What is claimed is:

1. A method for producing biodiesel, comprising:
   (1) providing a recombinant *C. rugosa* lipase comprising a sequence having at least 90% of identity to and the same activity as one of SEQ ID NOs: 1 to 4;
   (2) reacting the recombinant *C. rugosa* lipase with a non-edible oil in the presence of a first alcoholic solution; and
   (3) isolating the biodiesel from the reacted solution,
   wherein the non-edible oil is at least one selected from the group consisting of *Jatropha* oil, Karanja oil and castor oil, and the first alcoholic solution is at least one selected from the group consisting of methanol, ethanol, propanol, isopropanol and butanol.

2. The method of claim 1, wherein the recombinant *C. rugosa* lipase comprises a sequence of one of SEQ ID NOs. 1 to 4.

3. The method of claim 1, wherein the recombinant *C. rugosa* lipase is obtained by an expression in recombinant *Pichia pastoris*.

4. The method of claim 1, wherein in step (2), a dose of the recombinant *C. rugosa* lipase is from 40 U to 160 U per gram of the non-edible oil.

5. The method of claim 1, wherein in step (2), a molar concentration ratio of the non-edible oil to the first alcoholic solution is from 1:3 to 1:4.5 when the reaction starts.

6. The method of claim 1, wherein the reactants in step (2) comprise the recombinant *C. rugosa* lipase, the non-edible oil, the first alcoholic solution and water, and a content of the water is from 30 wt % to 50 wt % based on a weight of the reactants.

7. The method of claim 1, wherein step (2) is performed at a temperature of from 10° C. to 37° C.

8. The method of claim 1, wherein step (2) is performed for a reaction time of from 4 to 72 hours.

9. The method of claim 1, wherein step (2) further comprises adding a second alcoholic solution to the first alcoholic solution after the reaction starts.

10. The method of claim 9, wherein the second alcoholic solution is added within 8 to 24 hours after the reaction starts.

11. The method of claim 9, wherein the second alcoholic solution is the same as the first alcoholic solution.

12. The method of claim 1, wherein the recombinant *C. rugosa* lipase is in a form of an enzyme solution.

13. The method of claim 1, wherein the first alcoholic solution is methanol.

14. The method of claim 1, wherein the biodiesel is a fatty acid methyl ester.

15. The method of claim 1, further comprising step (4) recycling a residual solution containing the recombinant *C. rugosa* lipase after isolating the biodiesel.

16. A method for producing biodiesel, comprising:
   (1) providing a recombinant *C. rugosa* lipase comprising a sequence having at least 90% of identity to and the same activity as one of SEQ ID NOs: 1 to 4;
   (2) reacting the recombinant *C. rugosa* lipase with a non-edible oil in the presence of a first alcoholic solution at a temperature of from 10° C. to 37° C., and a molar concentration ratio of the non-edible oil to the first alcoholic solution is from 1:3 to 1:4.5 when the reaction starts; and
   (3) isolating the biodiesel from the reacted solution,
   wherein the non-edible oil is at least one selected from the group consisting of *Jatropha* oil, Karanja oil and castor oil, and the first alcoholic solution is at least one selected from the group consisting of methanol, ethanol, propanol, isopropanol and butanol.

17. The method of claim 16, wherein reactants in step (2) comprise the recombinant *C. rugosa* lipase, the non-edible oil, the first alcoholic solution and water, and a content of the water is from 30 wt % to 50 wt % based on a weight of the reactants.

18. The method of claim 16, wherein the recombinant *C. rugosa* lipase is obtained by an expression in recombinant *Pichia pastoris*, and the first alcoholic solution is methanol.

19. The method of claim 16, wherein step (2) further comprises adding the second alcoholic solution to the first alcoholic solution within 8 to 24 hours after the reaction starts.

* * * * *